(12) United States Patent
Bollier

(10) Patent No.: US 10,702,426 B2
(45) Date of Patent: Jul. 7, 2020

(54) INDIVIDUAL PULL TAB PACKAGING FOR TAMPONS

(71) Applicant: Laura Bollier, Sandy Springs, GA (US)

(72) Inventor: Laura Bollier, Sandy Springs, GA (US)

( * ) Notice: Subject to any disclaimer, the term of this patent is extended or adjusted under 35 U.S.C. 154(b) by 0 days.

(21) Appl. No.: 16/025,881

(22) Filed: Jul. 2, 2018

(65) Prior Publication Data

US 2020/0000651 A1    Jan. 2, 2020

(51) Int. Cl.
*A61F 13/20* (2006.01)
*A61F 13/551* (2006.01)
*B65D 77/32* (2006.01)
*A61F 13/84* (2006.01)

(52) U.S. Cl.
CPC ........ *A61F 13/55175* (2013.01); *A61F 13/20* (2013.01); *A61F 13/84* (2013.01); *B65D 77/32* (2013.01); *A61F 2013/55195* (2013.01); *A61F 2013/8497* (2013.01)

(58) Field of Classification Search
CPC .... B65D 77/32; A61F 13/55175; A61F 13/20; A61F 13/84; A61F 2013/55195; A61F 2013/8497
USPC ............... 206/440, 441, 823; 229/201, 235; 604/385.02, 904
See application file for complete search history.

(56) References Cited

U.S. PATENT DOCUMENTS

| | | | | |
|---|---|---|---|---|
| 3,892,310 A | * | 7/1975 | Welin-Berger | B65D 3/262 206/210 |
| 4,170,305 A | * | 10/1979 | Hull, Jr. | A61F 15/003 229/87.05 |
| 4,606,462 A | * | 8/1986 | Bogren | B65D 77/30 229/125.18 |
| 6,375,069 B1 | * | 4/2002 | Smith | B65D 3/262 229/211 |
| 2005/0167307 A1 | * | 8/2005 | Cheng | A45D 40/00 206/385 |
| 2009/0069769 A1 | * | 3/2009 | Minoguchi | A61F 13/34 604/385.02 |
| 2010/0130953 A1 | * | 5/2010 | Fung | A61F 15/003 604/385.02 |
| 2015/0144517 A1 | * | 5/2015 | Allen | B65D 51/245 206/459.5 |

* cited by examiner

*Primary Examiner* — Luan K Bui
(74) *Attorney, Agent, or Firm* — Charlena Thorpe, Esq.; Incorporating Innovation LLC

(57) ABSTRACT

Implementations of an individual pull tab packaging for tampons are provided. In some implementations, the individual pull tab packaging for tampons comprises a hollow elongated having a cylindrical shape configured to hold and enclose a tampon in an interior and comprising a top portion and a bottom portion joined together by a separable pull tab to open the interior, wherein the pull tab is configured to be pulled from the top portion and the bottom portion to disjoin the top portion and the bottom portion to open the interior.

8 Claims, 4 Drawing Sheets

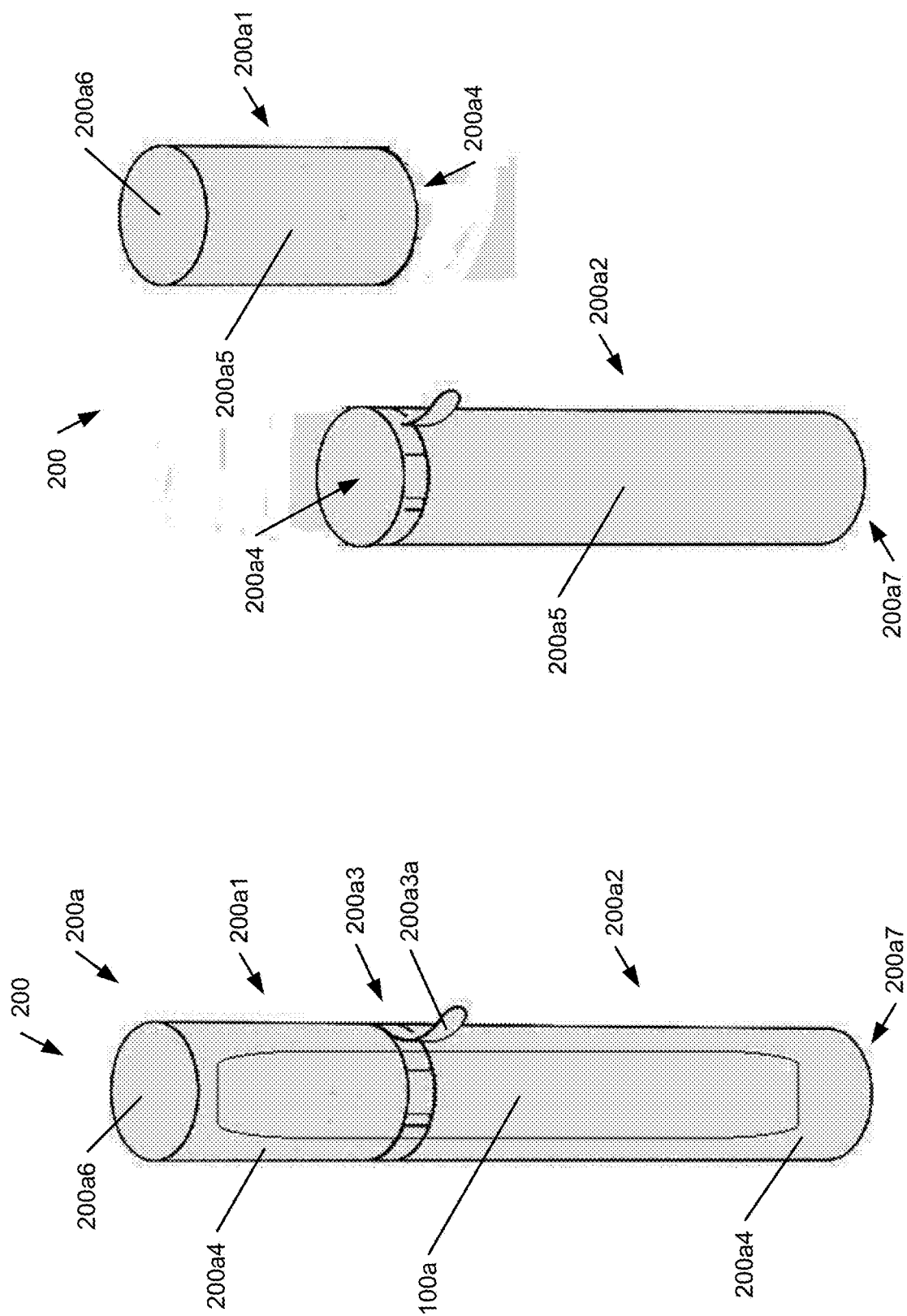

INDIVIDUAL PULL TAB PACKAGING FOR TAMPONS

TECHNICAL FIELD

This disclosure relates to implementations of individual pull tab packaging for tampons.

BACKGROUND

FIG. 1A illustrates a standard feminine hygiene product in the form of a tampon and FIG. 1B illustrates typical individual packaging for tampons. A tampon may be carried by a person in their hand, a purse or other handbag, or in a clothing pocket. However, individually carried feminine hygiene products provide little or no discretion or privacy because such products are easily noticeable due to their minimal and recognizably packaging. Furthermore, individually carried feminine hygiene products have little protection from damage such as bending or crushing, since the products are minimally packaged in paper or thin plastic wrapping as shown in FIG. 1B.

BRIEF DESCRIPTION OF THE DRAWINGS

FIGS. 2A-2D illustrate implementations of an example individual pull tab packaging for tampons according to the present disclosure.

DETAILED DESCRIPTION

Implementations of an individual pull tab packaging for tampons are provided. In some implementations, the individual pull tab packaging for tampons comprises a hollow elongated cylinder configured to hold and enclose a tampon in an interior and comprising a top portion and a bottom portion joined together by a pull tab and separable to open the interior, wherein the pull tab is configured to be pulled from the top portion and the bottom portion to disjoin the top portion and the bottom portion to open the interior.

In some implementations, a method for using the individual pull tab packaging for tampons comprises pulling the pull tab from the top portion and the bottom portion of the cylinder to disjoin the top portion and the bottom portion, separating the top portion and the bottom portion to open the interior of the cylinder, and removing a tampon from the interior of the cylinder.

In some implementations, the individual pull tab packaging for tampons is configured to have an external appearance that looks like a make-up or cosmetics container. For example, in some implementations, the individual pull tab packaging for tampons is configured to have an external appearance that looks like a lipstick or mascara container. For example, in some implementations, the packaging for tampons includes a top portion and bottom portion that are both elongated, cylindrical, and hollow where the top portion and bottom portion are separable similar to lipstick, lip gloss, mascara, concealer, etc. In this way, in some implementations, the individual pull tab packaging for tampons provides discretion and/or privacy for carrying individual tampons on-person, such as in a purse, pocketbook, or other handbag or in a clothing pocket.

In some implementations, the individual pull tab packaging for tampons is configured to have a sanitary interior to hold and enclose a tampon without the need for any additional packaging enclosing the tampon within the interior, such as an unpackaged tampon. In this way, in some implementations, the individual pull tab packaging for tampons provides a sanitary packaging to hold and enclose a tampon, including an unpackaged tampon.

In some implementations, the individual pull tab packaging for tampons is composed of cardboard or other similar material to hold and enclose a tampon. In this way, in some implementations, the individual pull tab packaging for tampons provides a protective packaging from damage such as bending or crushing for an unpackaged or minimally packaged tampon, such as in paper or thin plastic wrapping, that is carried on-person, such as in a purse, pocketbook, or other handbag or in a clothing pocket.

Figure 1B:
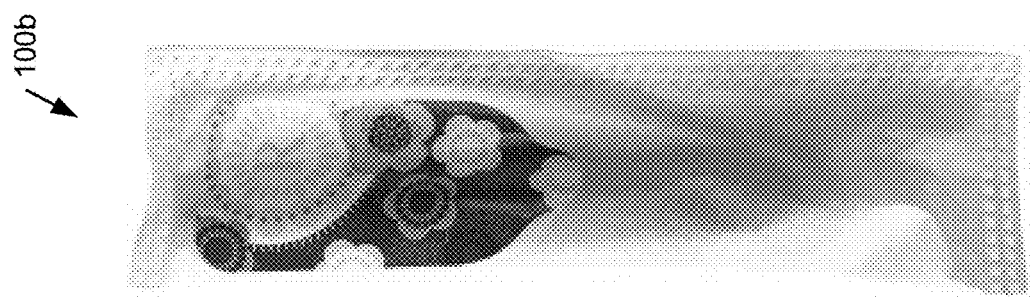
FIG. 1B illustrates an existing example of a minimal packaging for an existing tampon such as the tampon shown in FIG. 1A.
Figure 1A:
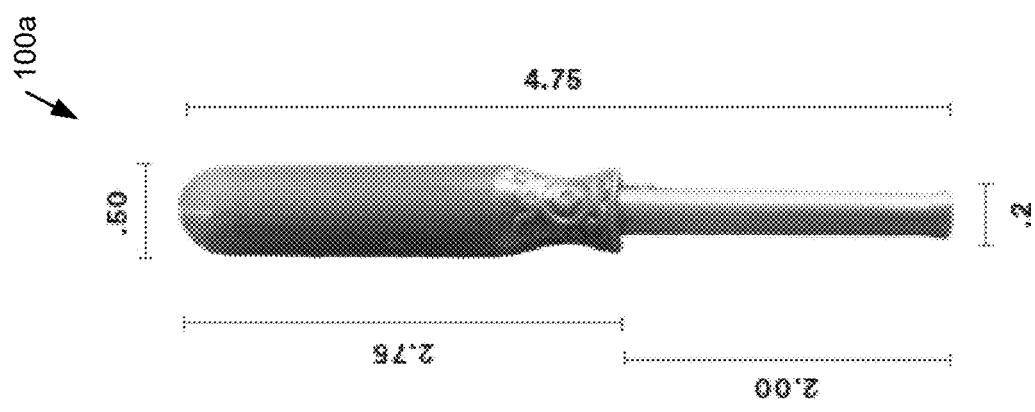
FIG. 1A illustrates an example existing unpackaged tampon that can be held and enclosed in implementations of example individual pull tab packaging for tampons according to the present disclosure.
Figure 2B:
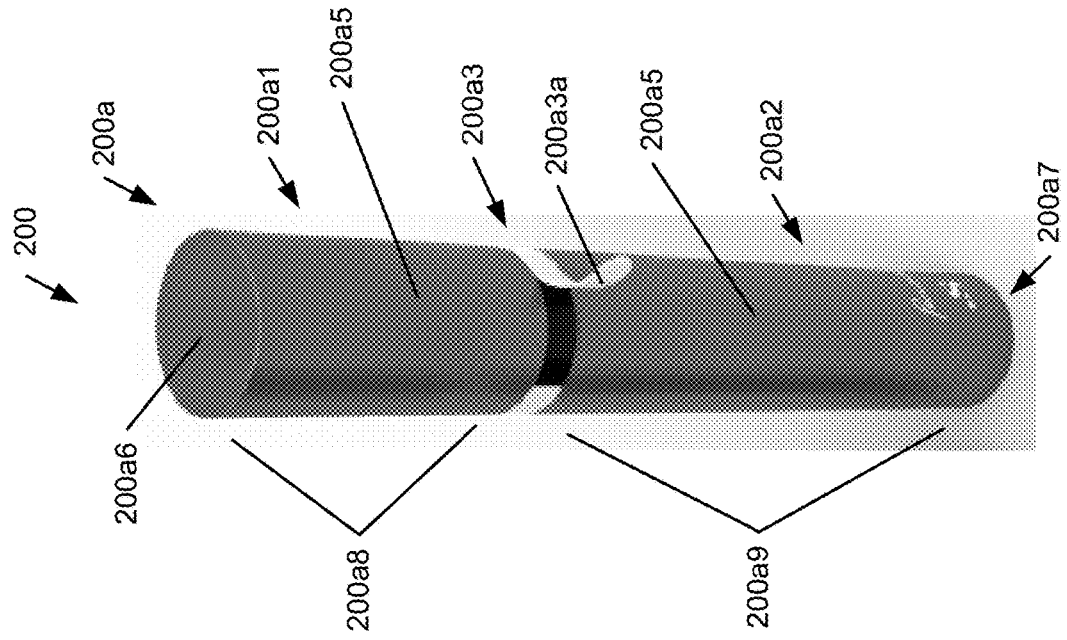
Figure 2A:
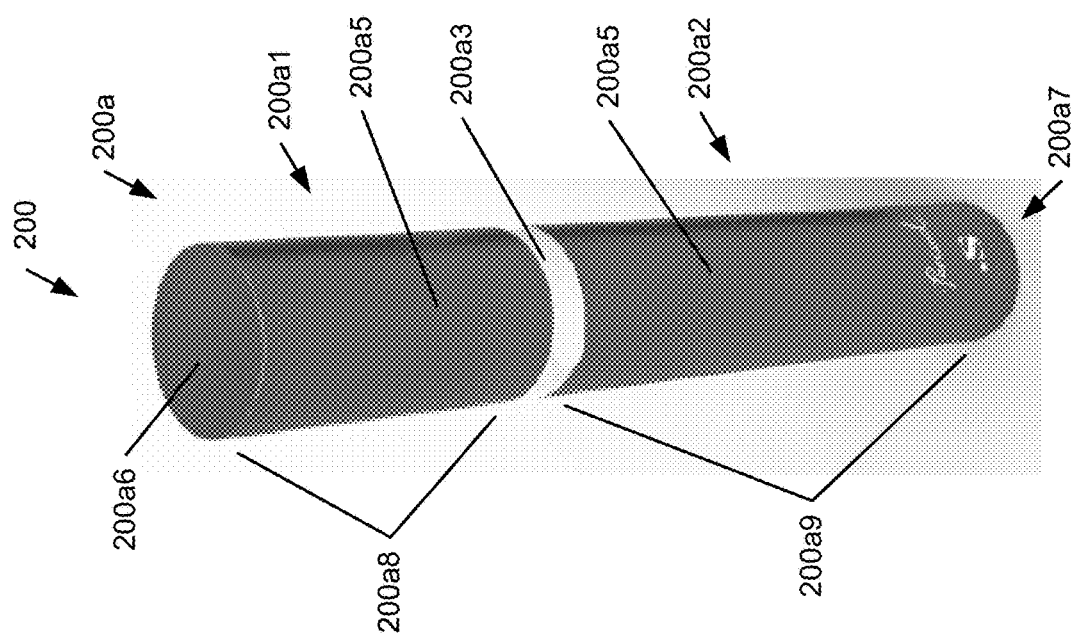

FIG. 1A illustrates an example existing unpackaged tampon 100a that can be held and enclosed in implementations of example individual pull tab packaging for tampons according to the present disclosure. Feminine hygiene products, such as the tampon 100a, are carried individually on-person, such as in a purse, pocketbook, or other handbag or in a clothing pocket. However, such individually carried feminine hygiene products 100a are easily noticeable and provide little or no discretion or privacy, since such products are either unpackaged or minimally and recognizably packaged (e.g., as shown in FIG. 1B).

FIG. 1B illustrates an existing example of a minimal packaging 100b for an existing tampon such as the tampon 100a shown in FIG. 1A. Such minimal packaging 100b is usually a paper or thin plastic wrapping. Such minimal packaging 100b is usually recognizable and/or provides little or no discretion or privacy. Such minimal packaging 100b provides little or no protection to a tampon 100a from damage such as bending or crushing when carried on-person, such as in a purse, pocketbook, or other handbag or in a clothing pocket.

FIGS. 2A-2D illustrate implementations of an example individual pull tab packaging for tampons 200 according to the present disclosure. In some implementations, the individual pull tab packaging for tampons 200 comprises a hollow elongated cylinder 200a that comprises a top portion 200a1, a bottom portion 200a2, and a pull tab 200a3.

As shown in FIG. 2C, in some implementations, the cylinder 200a is configured to hold and enclose a tampon 100a in an interior 200a4 of the cylinder 200a. For example, in some implementations, the cylinder 200a is configured to house and store a tampon 100a in the sealed or otherwise closed interior 200a4 of the cylinder 200a.

In some implementations, the interior 200a4 of the cylinder 200a is defined by an inner surface of a cylindrical surface 200a5 of the cylinder 200a that extends between an inner surface of a top base 200a6 and an inner surface of a bottom base 200a7 of the cylinder 200a. In some implementations, the interior 200a4 is sanitary, sterile, or otherwise uncompromised to hold and enclose the tampon 100a without any additional packaging enclosing the tampon 100a within the interior 200a4. In some implementations, the tampon 100a may comprise additional packaging.

In some implementations, the cylinder 200a is configured to have an external appearance that looks like a make-up container or cosmetics container. For example, in some implementations, the cylinder 200a is configured to have an external appearance that looks like a lipstick container or a mascara container.

In some implementations, the top portion 200a1 comprises the top base 200a6 and a first portion 200a8 of the cylindrical surface 200a5 extending from the top base 200a6. In some implementations, the bottom portion 200a2 comprises the bottom base 200a7 and a second portion 200a9 of the cylindrical surface 200a5 extending from the bottom base 200a7.

In some implementations, the bottom base 200a7 is configured to support the cylinder 200a on a surface to stand in an upright or vertical position with the top base 200a6 facing upward. For example, in some implementations, the bottom base 200a7 is flat. In some implementations, the bottom base 200a7 is configured to support the bottom portion 200a2 on a surface to stand in an upright or vertical position. In some implementations, the top base 200a6 is configured to support the top portion 200a1 on a surface to stand in an upright or vertical position. For example, in some implementations, the top base 200a6 is flat. In some implementations, the top base 200a6 and/or bottom base 200a7 are not flat.

In some implementations, the top portion 200a1 and the bottom portion 200a2 are sealed or otherwise joined together by the pull tab 200a3 to form the cylinder 200a. In some implementations, the pull tab 200a3 is a portion of the cylinder 200a that is a piece or strip of material that is separable from the top portion 200a1 and the bottom portion 200a2 of the cylinder 200a. In some implementations, the pull tab 200a3 extends around a portion of the outer surface of the cylinder 200a. In some implementations, the top portion 200a1 and the bottom portion 200a2 are separable to access the interior 200a4 of the cylinder 200a, as shown in FIG. 2D. In some implementations, the pull tab 200a3 is configured to be pulled from the top portion 200a1 and the bottom portion 200a2 to disjoin the top portion 200a1 and the bottom portion 200a2 to open the interior 200a4 of the cylinder 200a. In some implementations, the pull tab 200a3 includes a distal end portion 200a3a' configured to be pulled to separate the pull tab 200a3 from the top portion 200a1 and bottom portion 200a2.

In some implementations, the cylindrical surface 200a5 is perforated between the top portion 200a1 and the pull tab 200a3. In some implementations, the cylindrical surface 200a5 is perforated between the bottom portion 200a2 and the pull tab 200a3. In this way, in some implementations, the pull tab 200a3 can be torn from the top portion 200a1 and the bottom portion 200a2 to disjoin the top portion 200a1 and the bottom portion 200a2 to open the interior 200a4 of the cylinder 200a.

In some implementations, the pull tab 200a3 is adhesively attached to the top portion 200a1 and the bottom portion 200a2. In some implementations, the adhesive attachment is configured to allow the pull tab 200a3 to be pulled from the top portion 200a1 and the bottom portion 200a2 to disjoin the top portion 200a1 and the bottom portion 200a2 to open the interior 200a4 of the cylinder 200a.

In some implementations, the pull tab 200a3 is connected to the top portion 200a1 and the bottom portion 200a2 in any other suitable manner that allows the pull tab 200a3 to have the above described functionality.

In some implementations, the interior 200a4 of the cylinder 200a is resealable or otherwise recloseable so that the cylinder 200a can be used to store or discard the tampon 100a after it is used.

Figure 3:
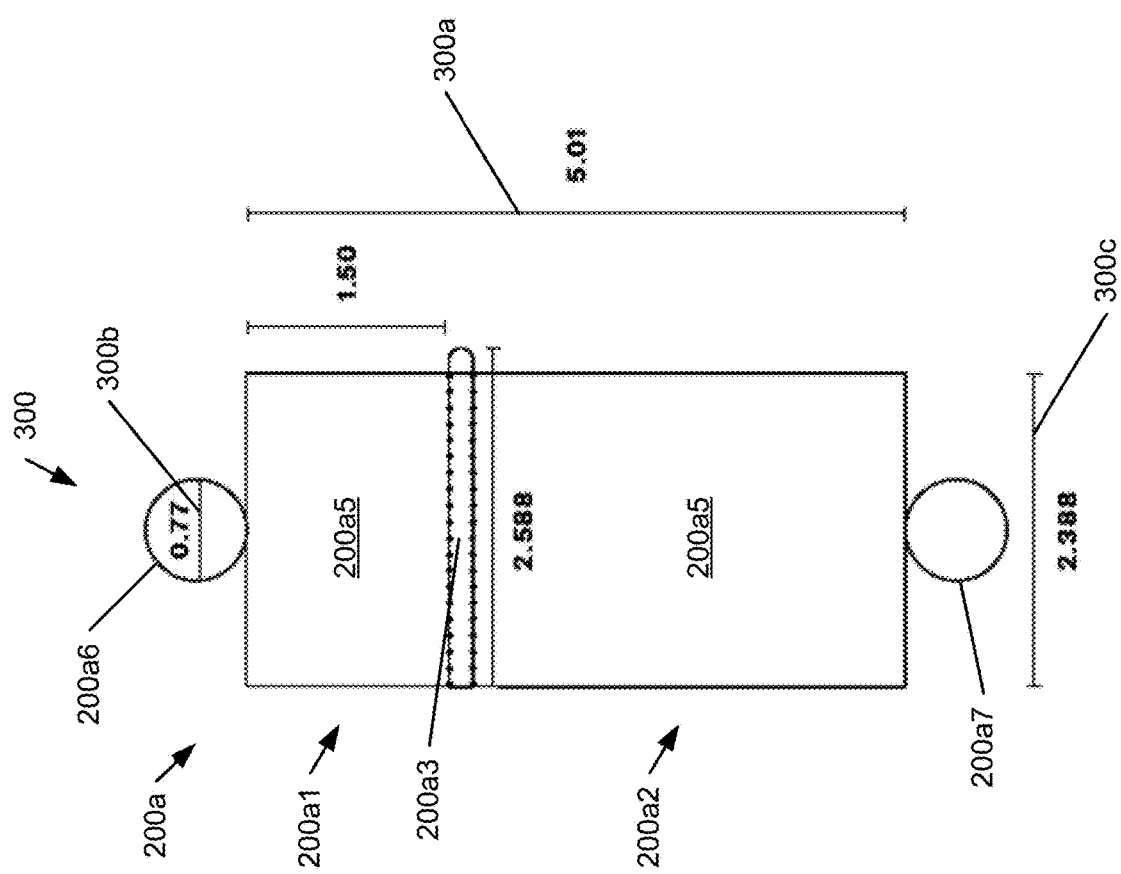
FIG. 3 illustrates an example fabrication layout of the individual pull tab packaging for tampons shown in FIGS. 2A-2D.

FIG. 3 illustrates an example fabrication layout or pattern 300 of the individual pull tab packaging for tampons 200 shown in FIGS. 2A-2D. FIG. 3 illustrates the cylinder 200a in a flattened position prior to fabrication. As shown in FIG. 3, in some implementations, the pull tab 200a3 is longer than the circumference of the cylinder 200a. In some implementations, the fabrication layout 300 includes components of the packaging 200 shown in and described above for FIGS. 2A-2D. In some implementations, the fabrication layout 300 also includes example dimensions in dimensions of the components of the packaging 200, such as the height 300a, the width 300b, and the circumference 300c of the cylinder 200a and the diameter 300b of the top base 200a6 and the bottom base 200a7.

As shown in FIG. 3, in some implementations, the height 300a of the cylinder 200a is greater than the width 300b of the cylinder 200a. In some implementations, the interior 200a4 of the cylinder 200a is sized to contain the tampon 100a. In some implementations, the cylinder 200a is sized to fit inside of a handbag, such as a purse or a pocketbook, or inside of a clothing pocket. In some implementations, one or more of the components of the individual pull tab packaging for tampons 200 comprises any other suitable dimensions, such as the dimensions indicated in FIG. 3. In some implementations, one or more of the components of the individual pull tab packaging for tampons 200 comprises dimensions less than the dimensions indicated in FIG. 3. In some implementations, one or more of the components of the individual pull tab packaging for tampons 200 comprises dimensions greater than the dimensions indicated in FIG. 3.

In some implementations, the individual pull tab packaging for tampons 200 is composed of any suitable materials. For example, in some implementations, the packaging 200 is composed of cardboard or similar material.

In some implementations, the individual pull tab packaging for tampons 200 can have any suitable appearance. For example, in some implementations, as discussed above, the packaging 200 can have an external appearance that looks like a make-up or cosmetics container such as a lipstick or mascara container.

In some implementations, an example method of using the individual pull tab packaging for tampons 200 comprises pulling the pull tab 200a3 from the top portion 200a1 and the bottom portion 200a2 of the cylinder 200a to disjoin the top portion 200a1 and the bottom portion 200a2. In some implementations, the method comprises separating the top portion 200a1 and the bottom portion 200a2 to access the interior 200a4 of the cylinder 200a. In some implementations, the method comprises removing the tampon 100a from the interior 200a4 of the cylinder 200a.

In some implementations, the method further comprises inserting the tampon 100a into the interior 200a4 of the cylinder 200a after the tampon 100a is used. In some implementations, the method further comprises resealing or otherwise reclosing the interior 200a4 of the cylinder 200a to store or discard the used tampon 100a.

In some implementations, the top portion and bottom portion can be sealed or otherwise joined together in any other manner other than a pull tap. For example, the top portion and bottom portion may be sealed or otherwise joined together by friction fit, screwing, etc. without the pull tab.

The figures, including photographs and drawings, comprised herewith may represent one or more implementations of the individual pull tab packaging for tampons.

Details shown in the figures, such as dimensions, descriptions, etc., are exemplary, and there may be implementations of other suitable details according to the present disclosure.

Reference throughout this specification to "an embodiment" or "implementation" or words of similar import means that a particular described feature, structure, or characteristic is comprised in at least one embodiment of the present invention. Thus, the phrase "in some implementations" or a phrase of similar import in various places throughout this specification does not necessarily refer to the same embodiment.

Many modifications and other embodiments of the inventions set forth herein will come to mind to one skilled in the art to which these inventions pertain having the benefit of the teachings presented in the foregoing descriptions and the associated drawings.

The described features, structures, or characteristics may be combined in any suitable manner in one or more embodiments. In the above description, numerous specific details are provided for a thorough understanding of embodiments of the invention. One skilled in the relevant art will recognize, however, that embodiments of the invention can be practiced without one or more of the specific details, or with other methods, components, materials, etc. In other instances, well-known structures, materials, or operations may not be shown or described in detail.

While operations may be depicted in the drawings in a particular order, this should not be understood as requiring that such operations be performed in the particular order shown or in sequential order, or that all illustrated operations be performed, to achieve desirable results.

The invention claimed is:

1. An individual pull tab packaging for a tampon comprising:
   a top section;
   a bottom section; and
   a hollow elongated housing having a cylindrical shape extending from the top section to the bottom section wherein the interior surface of the top section, the interior surface of the hollow elongated housing, and the interior surface of the bottom section define a closed interior of the packaging, wherein the closed interior of the packaging is configured to hold and enclose a tampon, further wherein:
   the hollow elongated housing comprises a top portion, a bottom portion, and a separable strip of material wherein the top portion of the hollow elongated housing and the bottom portion of the hollow elongated housing are separably joined together by the separable strip of material;
   the top portion of the hollow elongated housing is defined by the top section and a first portion of the hollow elongated housing having a first outermost edge wherein the top portion extends from the top section to the first outmost edge;
   the bottom portion of the hollow elongated housing is defined by the bottom section and a second portion of the hollow elongated housing having a second outermost edge wherein the bottom portion extends from the bottom section to the second outmost edge;
   the separable strip comprises a portion of the hollow elongated housing positioned between the first outermost edge of the top portion and the second outermost edge of the bottom portion wherein the separable strip comprises a top edge and a bottom edge opposite the top edge and wherein the top edge of the separable strip is removably adjoined to the first outermost edge of the top portion and the bottom edge of the separable strip is removable adjoined to the second outermost edge of the bottom portion;
   the top edge of the separable strip and the outermost edge of the top portion is perforated and the bottom edge of the separable strip and the second outermost edge of the bottom portion is perforated to allow the separable strip of material to be pulled from the top portion and the bottom portion to disjoin the top portion and the bottom portion to access the closed interior of the packaging;
   the packaging is configured such that when the separable strip of material is pulled from the top portion and the bottom portion of the hollow elongated housing, the top portion and bottom portion are disjoined and the interior of the packaging is accessible to remove a tampon housed within the packaging; and
   the closed interior of the cylinder is recloseable after the top portion and bottom portion are disjoined and the tampon is removed wherein the packaging is configured to bring the top portion and the bottom portion together to define a closed interior.

2. The individual pull tab packaging for tampons of claim 1 further comprising the tampon held and enclosed within the closed interior of the packaging.

3. The individual pull tab packaging for tampons of claim 1 wherein the closed interior of the packaging is sterile to hold and enclose a tampon without any additional packaging enclosing the tampon within the interior.

4. The individual pull tab packaging for tampons of claim 1 wherein the bottom section is configured to support the remainder of the packaging to stand in an upright or vertical position with the top section facing upward.

5. The individual pull tab packaging for tampons of claim 1 wherein the packaging is composed of cardboard.

6. A method of using the individual pull tab packaging for a tampon of claim 2, the method comprising:
   pulling the separable strip of material from the top portion and the bottom portion of the hollow elongated housing to disjoin the top portion and the bottom portion of the hollow elongated housing;
   separating the top portion and the bottom portion of the hollow elongated housing to access the interior of the packaging; and
   removing the tampon from the interior of the cylinder.

7. The method of claim 6 wherein the interior of the packaging is recloseable, the method further comprising:
   inserting a used tampon into the interior of packaging; and
   reclosing the interior of the packaging to store or discard the used tampon.

8. An individual packaging for a tampon comprising:
   a top section;
   a bottom section; and
   a hollow elongated housing having a cylindrical shape extending from the top section to the bottom section wherein the interior surface of the top section, the interior surface of the hollow elongated housing, and the interior surface of the bottom section define a closed interior of the packaging, wherein the closed interior of the packaging is configured to hold and enclose a tampon, further wherein:
   the hollow elongated housing comprises a top portion, a bottom portion, and a separable strip of material wherein the top portion of the hollow elongated housing and the bottom portion of the hollow elongated housing are separably joined together by the separable strip of material;

the top portion of the hollow elongated housing is determined by the top section and a first portion of the hollow elongated housing having a first outermost edge wherein the top portion extends from the top section to the first outmost edge;

the bottom portion of the hollow elongated housing is defined by the bottom section and a second portion of the hollow elongated housing having a second outermost edge wherein the bottom portion extends from the bottom section to the second outmost edge;

the separable strip comprises a portion of the hollow elongated housing positioned between the first outermost edge of the top portion and the second outermost edge of the bottom portion wherein the separable strip comprises a top edge and a bottom edge opposite the top edge and wherein the top edge of the separable strip is removably adjoined to the first outermost edge of the top portion and the bottom edge of the separable strip is removably adjoined to the second outermost edge of the bottom portion to allow the separable strip of material to be pulled from the top portion and the bottom portion to disjoin the top portion and the bottom portion to access the closed interior of the packaging;

the packaging is configured such that when the separable strip of material is pulled from the top portion and the bottom portion of the hollow elongated housing, the top portion and bottom portion are disjoined and the interior of the packaging is accessible to remove a tampon housed within the packaging; and the closed interior of the cylinder is reclosable after the top portion and bottom portion are disjoined and the tampon is removed wherein the packaging is configured to bring the top portion and the bottom portion together to define a closed interior.

* * * * *